United States Patent [19]
Kühle et al.

[11] 3,947,513
[45] Mar. 30, 1976

[54] N-SULFINYL-N'-ARYL-HYDRAZINES

[75] Inventors: Engelbert Kühle, Berg. Gladbach; Erich Klauke, Odenthal-Hahnenberg; Paul-Ernst Frohberger, Leverkusen, all of Germany

[73] Assignee: Bayer Aktiengesellschaft, Leverkusen, Germany

[22] Filed: Sept. 4, 1973

[21] Appl. No.: 394,365

[30] Foreign Application Priority Data
Sept. 12, 1972 Germany............................ 2244616

[52] U.S. Cl. .......... 260/551 S: 260/501.21; 260/569; 424/320
[51] Int. Cl.² ....................................... C07C 145/02
[58] Field of Search .......... 260/565, 551 S; 424/330

[56] References Cited
UNITED STATES PATENTS

| | | | |
|---|---|---|---|
| 2,888,483 | 5/1959 | Rudner et al. .................. | 260/551 X |
| 2,898,265 | 8/1959 | Wegler et al. .................. | 260/551 X |
| 3,236,842 | 2/1966 | Klauke et al. .................. | 260/551 X |

OTHER PUBLICATIONS
Burges, "Medicinal Chemistry," 3rd Ed., Part 1, pp. 71–72 (1970).

*Primary Examiner*—Robert V. Hines
*Attorney, Agent, or Firm*—Burgess, Dinklage & Sprung

[57] ABSTRACT

N-sulfinyl-N'-aryl-hydrazines of the formula

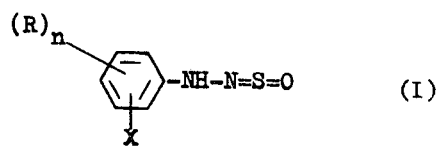

(I)

in which
X is trifluoromethyl or trifluoromethoxy,
n is 0, 1 or 2, and
R is methyl, trifluoromethyl, methoxy or halogen, which possess fungicidal properties.

8 Claims, No Drawings

N-SULFINYL-N'-ARYL-HYDRAZINES

The present invention relates to and has for its objects the provision of particular new N-sulfinyl-N'-aryl-hydrazines, i.e. N-sulfinyl-N'-(trifluoromethyl or trifluoromethoxy)-phenyl-hydrazines, which are optionally methyl, methoxy or halogen-substituted on the benzene ring, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

German Patent Specification No. 1,059,706 discloses that certain N-sulfinyl-N'-aryl-hydrazines, wherein the aryl radical is an optionally substituted benzene, naphthalene or heterocyclic radical, can be used as agents for combating mites, but these compounds are fungicidally inactive.

The present invention provides, as new compounds, the N-sulfinyl-N'-aryl-hydrazines of the general formula

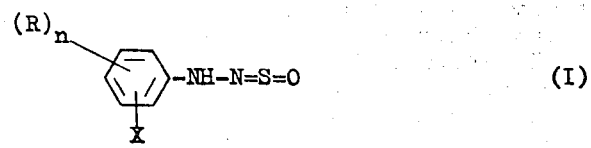

in which
X is trifluoromethyl or trifluoromethoxy,
n is 0, 1 or 2, and
R is methyl, trifluoromethyl, methoxy or halogen.
Preferably X is trifluoromethyl or trifluoromethoxy;
R is chlorine or methyl; and n is 0 or 1.

It is distinctly surprising that the compounds according to the invention, in contrast to the known acaricidally active N-sulfinyl-N'-aryl-hydrazines, possess a pronounced fungicidal activity and even surpass the standard preparation zinc ethylene-bis-dithiocarbamate. They thus represent an enrichment of the art.

The present invention also provides a process for the preparation of an N-sulfinyl-N'-aryl-hydrazine of the formula (I) in which an aryl-hydrazine of the general formula

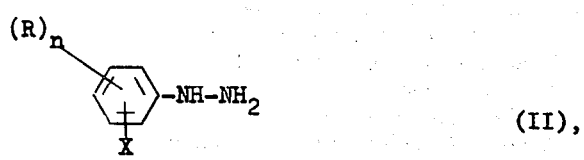

in which
X, R and n have the above-mentioned meanings, is reacted with a sulfinylaniline in the presence of a diluent.

When using 3-trifluoromethyl-phenyl-hydrazine and sulfinylaniline as the starting materials, the course of the reaction of the process can be represented by the following equation:

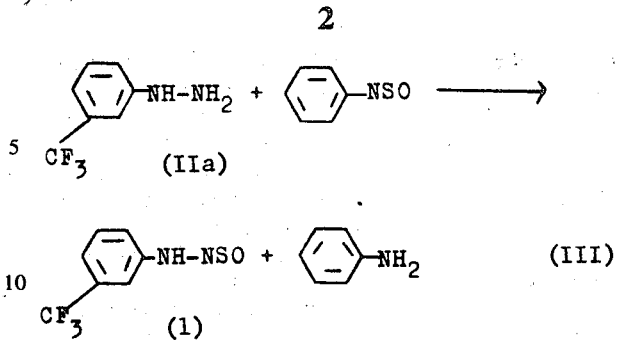

A number of the arylhydrazines of the formula (II) are known (see Tetrahedron 8, 67 (1960)); they can, however, all be prepared in a known manner, for example by diazotization and subsequent reduction of the corresponding anilines. As examples of the arylhydrazines which can be used according to the invention there may be mentioned: 2-, 3- or 4-tri-fluoromethyl-phenylhydrazine, 2-chloro- or 3-chloro-4-trifluoromethyl-phenylhydrazine, 4-chloro- or 6-chloro-3-trifluoromethyl-phenylhydrazine, 4-methoxy-3-trifluoromethyl-phenylhydrazine, 2,6-dichloro-4-trifluoromethyl-phenylhydrazine, 3-trifluoromethyl-4-methyl-phenylhydrazine, 3,5-bis-trifluoromethyl-phenylhydrazine and 4-trifluoromethoxy-phenylhydrazine.

As the sulfinylaniline required for the reaction, the parent substance itself (also called thionylaniline) is preferably used. This compound has been known for a long time (see, for example, Beilsteins Handbuch der Organischen Chemie (Beilstein's Handbook of Organic Chemistry), 4th edition, H 12, 578, I 293, II 309).

As diluents it is possible to use, in addition to water, lower alkanols, for example methanol or ethanol, or lower carboxylic acids such as acetic acid.

The reaction temperatures can be varied within a fairly wide range; in general, the reaction is effected at from 0° to 80°C, preferably from 10° to 50°C.

The arylhydrazines are used as such, or in the form of their acetates, for the reaction. It is, however, also possible to use the hydrochlorides or sulfates, with addition of sodium acetate. In carrying out the process, 1 mole of sulfinylaniline is preferably employed per mole of arylhydrazine. However, deviations therefrom by up to 30% are possible without significantly impairing the yield. In general, the sulfinylaniline is added dropwise to a solution of the arylhydrazine. The end product in most cases crystallizes out from the reaction solution and can be isolated by simple suction filtration or ordinary filtration.

The active compounds according to the invention show a high degree of fungitoxic activity and a broad effect and possess a relatively low toxicity to warm-blooded animals, which makes them simple to handle and permits their being used in practice for combating undesired fungal growth. Fungitoxic agents in plant protection are used for combating phytopathogenic fungi of the most diverse classes of fungus, for example Archimycetes, Phycomycetes, Ascomycetes, Basidiomycetes and Fungi Imperfecti.

The good toleration of the compounds by plants permits the use of the compounds against fungal diseases of plants, by treating the standing crop plant or individual parts thereof, or the seed or the culture soil. The active compounds are particularly effective against fungi which cause tracheomycosis, which attack the plants through the soil, such as varieties of Verticillium, varieties of Fusarium and varieties of Phialophora. However, they are also very effective against seed-borne fungi, such as *Tilletia tritici*, and against fungi which inhabit the soil, such as varieties of Rhizoctonia, varieties of Fusarium, varieties of Pythium and varieties of Thielaviopsis. Good effects are also noted against *Helmithosporium gramineum, Ustilago avenae, Botrytis cinerea* and *Fusicladium dendriticum*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, rodenticides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, a correspondingly combative or toxic amount, i.e. fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, slurry dressing, moist dressing, wet dressing and the like.

In the case of dressing, amounts of active compound of 10 mg to 10 g, preferably 100 mg to 3 g, are generally used per kilogram of seed. In the treatment of soil, which can be carried out over the entire surface, in strips or at points, active-compound concentrations of 1 to 1,000 g of active compound per m$^3$ of soil, preferably 10 to 200 g per m$^3$, are generally required at the place where the action is intended.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Agar plate test

Test for fungitoxic effectiveness and breadth of the activity spectrum.
Solvent: Acetone Parts by weight: a) 1,000; b) 100

To produce a suitable preparation of the active compound, 1 part by weight of the active compound was taken up in the stated amount of solvent.

The preparation of the active compound was added to potato dextrose agar (which had been liquefied by heating) in such an amount that the desired concentration of active compound was set up therein. After thorough shaking to achieve a uniform dispersion of the active compound, the agar was poured into Petri dishes under sterile conditions. When the mixture of substrate and active compound had solidified, test fungi from pure cultures were inoculated onto it in small discs of 5 mm diameter. The Petri dishes remained at 20°C for 3 days for incubation.

After this time, the inhibiting action of the active compound on the mycelium growth was determined in categories, taking into account the untreated control. The symbol "O" means no mycelium growth, either on the treated substrate or on the inoculum; the symbol "—" means mycelium growth on the inoculum only with no spread to the treated substrate; and the symbol "+" means mycelium growth from the inoculum onto the treated substrate, similar to the spread to the untreated substrate of the control.

The active compounds, the concentration of the active compounds, the test fungi and the inhibition effects achieved can be seen from the following table:

Table 1

| Active compound | Active compound concentration in the substrate in mg per litre | Corticium rolfsii | Sclerotinia sclerotiorum | Verticillium alboatrum | Thielaviopsis basicola | Phytophthora cactorum | Fusarium culmorum | Fusarium oxysporum | Fusarium solani f. pisi |
|---|---|---|---|---|---|---|---|---|---|
| untreated | — | + | + | + | + | + | + | + | + |
| (A) CH$_2$—NH—C(=S)—S\ Zn / CH$_2$—NH—C(=S)—S (known) | a) 10<br>b) 100 | +<br>0 | +<br>+ | +<br>+ | +<br>+ | +<br>0 | +<br>— | +<br>0 | +<br>+ |
| (1) CF$_3$—C$_6$H$_4$—NH—N=S=O | a) 10<br>b) 100 | 0<br>0 | —<br>0 | +<br>0 | —<br>0 | +<br>0 | —<br>0 | +<br>0 | +<br>— |
| (2) CF$_3$—C$_6$H$_4$—NH—N=S=O | a) 10<br>b) 100 | 0<br>0 | 0<br>0 | +<br>0 | 0<br>0 | +<br>+ | 0<br>0 | +<br>+ | +<br>+ |
| (3) Cl,CF$_3$—C$_6$H$_3$—NH—N=S=O | a) 10<br>b) 100 | 0<br>0 | 0<br>0 | +<br>+ | +<br>+ | +<br>+ | +<br>+ | +<br>+ | +<br>+ |

Table 1-continued

| Active compound | Active compound concentration in the substrate in mg per litre | Corticium rolfsii | Sclerotinia sclerotiorum | Verticillium alboatrum | Thielaviopsis basicola | Phytophthora cactorum | Fusarium culmorum | Fusarium oxysporum | Fusarium solani f. pisi |
|---|---|---|---|---|---|---|---|---|---|
| 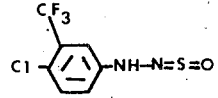 (4) | a) 10<br>b) 100 | 0<br>0 | 0<br>0 | +<br>+ | −<br>− | +<br>+ | +<br>+ | +<br>+ | +<br>+ |
| 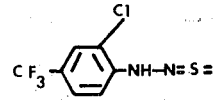 (5) | a) 10<br>b) 100 | 0<br>0 | +<br>0 | +<br>+ | −<br>− | +<br>+ | +<br>0 | +<br>+ | +<br>+ |
| 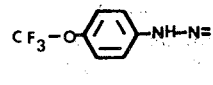 (6) | b) 100 | 0 | 0 | 0 | 0 | + | 0 | 0 | + |

EXAMPLE 2

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4°C for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18°C in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentrations of the active compounds in the dressing, the amounts of dressing used and the number of diseased plants can be seen from the following table:

Table 2

| Active compound | Seed dressing test/stripe disease of barley | | |
|---|---|---|---|
| | Active compound concentration in the dressing in % by weight | Amount of dressing used in g/kg of seed | Number of plants with stripe disease in % of the total emerged plants |
| without dressing | — | — | 32.6 |
| 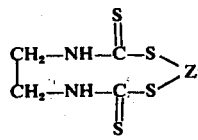<br>(known) (A) | 10<br>30 | 2<br>2 | 25.6<br>19.0 |
| 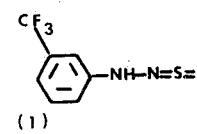<br>(1) | 3<br>10<br>30 | 2<br>2<br>2 | 5.6<br>1.1<br>0.0 |
| 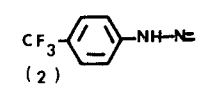<br>(2) | 3 | 2 | 5.3 |

Table 2-continued

Seed dressing test/stripe disease of barley

| Active compound | Active compound concentration in the dressing in % by weight | Amount of dressing used in g/kg of seed | Number of plants with stripe disease in % of the total emerged plants |
| --- | --- | --- | --- |
|  | 10 | 2 | 3.0 |
|  | 30 | 2 | 1.0 |
| 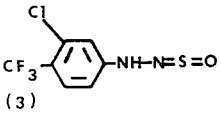 (3) | 3<br>10<br>30 | 2<br>2<br>2 | 2.2<br>0.0<br>0.0 |
| 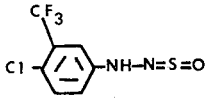 (4) | 3<br>10<br>30 | 2<br>2<br>2 | 5.2<br>2.1<br>0.0 |
|  (6) | 10<br>30 | 2<br>2 | 2.1<br>0.0 |

EXAMPLE 3

Seed dressing test/snow mold (seed-borne mycosis)

To produce a suitable dry dressing, the active compound was extended with a mixture of equal parts by weight of talc and kieselguhr to give a finely powdered mixture with the desired concentration of active compound.

To apply the dressing, rye seed, which was naturally infected by Fusarium nivale, was shaken with the dressing in a closed glass flask. Two batches of 100 grains of this seed were sown 1 cm deep in seed boxes containing Fruhstorfer standard soil. The young plants developed in climatic chambers at 10°C, at a relative atmospheric humidity of 95% and in diffused natural light; they showed the typical symptoms of snow mould within the first 3 weeks.

After this time, the number of Fusarium-infected plants was determined as a percentage of the total number of emerged plants. The smaller the number of diseased plants, the more effective was the active compound.

The active compounds, the concentrations of the active compounds in the dressing, the amounts of dressing used and the number of diseased plants can be seen from the following table:

Table 3

Seed dressing test/snow

| Active compound | Active compound concentration in the dressing in % by weight | Amount of dressing used in g/kg of seed | Number of Fusarium-infected plants in % of the total emerged plants |
| --- | --- | --- | --- |
| without dressing | — | — | 16.5 |
| 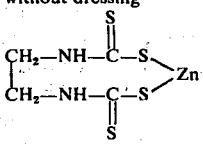 (known) (A) | 30 | 2 | 9.1 |
| 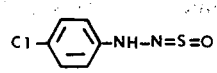 (known) (B) | 30 | 2 | 17.8 |

Table 3-continued

| Active compound | Seed dressing test/snow Active compound concentration in the dressing in % by weight | Amount of dressing used in g/kg of seed | Number of Fusarium-infected plants in % of the total emerged plants |
|---|---|---|---|
| 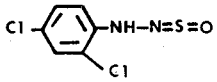 (known) (C) | 30 | 2 | 13.9 |
| 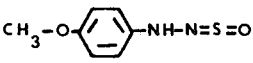 (known) (D) | 30 | 2 | 14.3 |
| 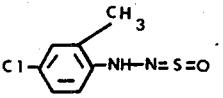 (known) (E) | 30 | 2 | 14.3 |
| 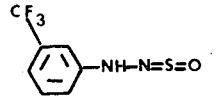 (1) | 30 | 2 | 1.6 |
| 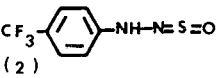 (2) | 10<br>30 | 2<br>2 | 4.8<br>0.5 |
| 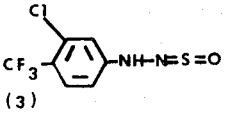 (3) | 10<br>30 | 2<br>2 | 3.5<br>0.0 |
| 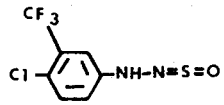 (4) | 3<br>10<br>30 | 2<br>2<br>2 | 3.4<br>1.0<br>0.0 |

EXAMPLE 4

Seed dressing test/loose smut of oats (Seed-borne mycosis)

To produce a suitable dry dressing, the active compound was extended with a mixture of equal parts by weight of talc and kieselguhr to give a finely powdered mixture with the desired concentration of active compound.

To apply the dressing, oat seed, which was naturally infested with loose smut (*Ustilago avenae*), was shaken with the dressing in a closed glass flask. Two batches of 100 grains of the seed were sown 2 cm deep in seed boxes containing a mixture of 1 part by volume of Fruhstorfer standard soil and 1 part by volume of quartz sand. The boxes were placed in a greenhouse at a temperature of about 18°C, kept normally moist and exposed to light for 16 hours daily. After 10 – 12 weeks, the oats flowered and showed healthy and diseased panicles (smutted panicles).

After this time, the number of diseased panicles was determined as a percentage of the total number of developed panicles. 0% means that no diseased panicles were present; 100% means that all the panicles were diseased. The fewer diseased panicles were formed, the more effective was the active compound.

The active compounds, the concentrations of the active compounds in the dressing, the amounts of dressing used and the number of diseased panicles can be seen from the following table:

Table 4

| Active compounds | Seed dressing test/loose smut of oats | | |
|---|---|---|---|
| | Active compound concentration in the dressing in % by weight | Amount of dressing used in g/kg of seed | Number of diseased panicles in % of the total number of developed panicles |
| without dressing | — | — | 45.1 |
| (known) (A) $CH_2-NH-C(=S)-S$ \ $CH_2-NH-C(=S)-S$ / Zn | 30 | 6 | 16.1 |
| (1) $CF_3$-C$_6$H$_4$-NH-N=S=O | 30 | 6 | 5.9 |
| (2) $CF_3$-C$_6$H$_4$-NH-N=S=O | 30 | 6 | 2.4 |

The process of this invention is illustrated in the following preparative Example.

EXAMPLE 5

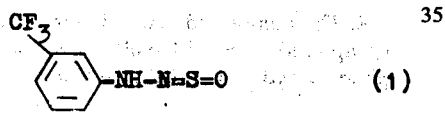

(1)

20 g (0.113 mole) of 3-trifluoromethyl-phenylhydrazine were dissolved in 50 ml of methanol with addition of 5 ml of acetic acid; 16 g (0.115 mole) of sulfinylaniline were added dropwise at a temperature of 22°C. The product crystallized out while the temperature rose to about 30°C. After filtration and drying, 16 g of N-sulfinyl-N-'-(3-trifluoromethylphenyl)-hydrazine of melting point 100°C were obtained. The yield was 64% of theory.

The following compounds were obtained by methods analogous to that described above.

| Compound No. | Formula | Melting point [°C] |
|---|---|---|
| (2) | $CF_3$-C$_6$H$_4$-NH-N=S=O | 140 |
| (3) | $CF_3$-C$_6$H$_3$(Cl)-NH-N=S=O | 158 |
| (4) | Cl-C$_6$H$_3$(CF$_3$)-NH-N=S=O | 148–149 |
| (5) | $CF_3$-C$_6$H$_3$(Cl)-NH-N=S=O | 46–47 |
| (6) | $CH_3$-O-C$_6$H$_4$-NH-N=S=O | 96–97 |

Other compounds which can be similarly prepared include:
N-sulfinyl-N'-[2,4,6-tris-(trifluoromethyl)phenyl]-hydrazine,
N-sulfinyl-N'-(2-methyl-4-trifluoromethoxyphenyl)-hydrazine,
N-sulfinyl-N'-(3-bromo-4-trifluoromethylphenyl)-hydrazine,
N-sulfinyl-N'-(2-methoxy-4-trifluoromethyl-6-chloro-phenyl)-hydrazine,
and the like.

It will be appreciated that the instant specification and examples are set forth by way of illustration and not limitation, and that various modifications and changes may be made without departing from the spirit and scope of the present invention.

What is claimed is:

1. An N-sulfinyl-N'-aryl-hydrazine of the formula

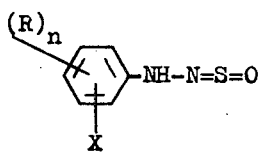
(I)

in which
X is trifluoromethyl or trifluoromethoxy,
n is 0, 1 or 2, and
R is methyl, trifluoromethyl, methoxy or halogen.

2. A compound according to claim 1, in which X is trifluoromethyl or trifluoromethoxy; R is chlorine or methyl; and n is 0 or 1.

3. The compound according to claim 1, wherein such compound is N-sulfinyl-N'-(3-trifluoromethylphenyl)-hydrazine of the formula

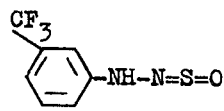
(1)

4. The compound according to claim 1, wherein such compound is N-sulfinyl-N'-(4-trifluoromethylphenyl)-hydrazine of the formula

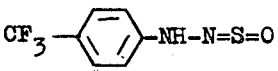
(2)

5. The compound according to claim 1, wherein such compound is N-sulfinyl-N'-(3-chloro-4-trifluoromethylphenyl)-hydrazine of the formula 6. The compound according to claim 1, wherein such compound is N-sulfinyl-N'-(3-trifluoromethyl-4-chlorophenyl)-hydrazine of the formula

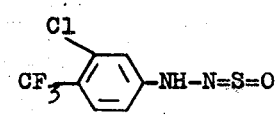
(3)

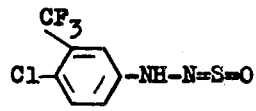
(4)

7. The compound according to claim 1, wherein such compound is N-sulfinyl-N'-(2-chloro-4-trifluoromethylphenyl)-hydrazine of the formula

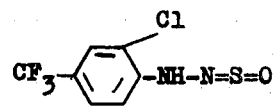
(5)

8. The compound according to claim 1, wherein such compound is N-sulfinyl-N'-(4-trifluoromethoxyphenyl)-hydrazine of the formula

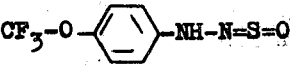
(6)

* * * * *